United States Patent
Kim et al.

(10) Patent No.: US 11,356,651 B2
(45) Date of Patent: Jun. 7, 2022

(54) HEAD MOUNT SYSTEM FOR PROVIDING SURGERY SUPPORT IMAGE

(71) Applicant: Korea University Research and Business Foundation, Seoul (KR)

(72) Inventors: Beop-Min Kim, Seoul (KR); Yong-Guk Kang, Seoul (KR); Ki-Hyeok Kwon, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/955,527

(22) PCT Filed: Dec. 6, 2018

(86) PCT No.: PCT/KR2018/015371
§ 371 (c)(1),
(2) Date: Jun. 18, 2020

(87) PCT Pub. No.: WO2019/146904
PCT Pub. Date: Aug. 1, 2019

(65) Prior Publication Data
US 2021/0006775 A1    Jan. 7, 2021

(30) Foreign Application Priority Data
Jan. 29, 2018    (KR) .......................... 10-2018-0010410

(51) Int. Cl.
*H04N 13/344*    (2018.01)
*H04N 13/239*    (2018.01)
(Continued)

(52) U.S. Cl.
CPC ......... *H04N 13/344* (2018.05); *A61B 90/361* (2016.02); *G02B 27/0172* (2013.01);
(Continued)

(58) Field of Classification Search
CPC .. H04N 13/344; H04N 13/194; H04N 13/239; H04N 13/346; H04N 13/161;
(Continued)

(56) References Cited

U.S. PATENT DOCUMENTS

2010/0113940 A1* 5/2010 Sen .................... A61B 5/742
                                                    600/476
2014/0002587 A1* 1/2014 Aguren ................ H04N 5/2254
                                                    348/36
(Continued)

FOREIGN PATENT DOCUMENTS

JP    2008-18015 A    1/2008
JP    2015-521913 A   8/2015
(Continued)

OTHER PUBLICATIONS

Search Report (PCT/ISA/210) dated Mar. 20, 2019, issued by the International Searching Authority for Application No. PCT/KR2018/015371.

*Primary Examiner* — Susan E. Hodges
(74) *Attorney, Agent, or Firm* — Sughrue Mion, PLLC

(57) ABSTRACT

The present invention relates to a head mount system for providing a surgery support image, the system including: a head mount body wearable on a user's head; a near-infrared camera installed on the head mount body and capturing near-infrared light; a near-infrared image projection unit installed on the head mount body and projecting a near-infrared image; a near-infrared image processing unit receiving a captured image taken by the near-infrared camera, generating the near-infrared image, and transmitting the near-infrared image to the near-infrared image projection unit; and a transparent optic system installed on the head mount body to be positioned in front of user's eyes when the head mount body is worn on the user's head, transmitting visible light to enable a user to see a user's front, reflecting
(Continued)

the near-infrared light coming from the user's front to the near-infrared camera to allow the near-infrared camera to capture the near-infrared light.

6 Claims, 10 Drawing Sheets

(51) Int. Cl.
| | |
|---|---|
| *H04N 13/194* | (2018.01) |
| *H04N 13/346* | (2018.01) |
| *H04N 5/33* | (2006.01) |
| *H04N 13/161* | (2018.01) |
| *G02B 27/01* | (2006.01) |
| *A61B 90/00* | (2016.01) |
| *A61B 90/50* | (2016.01) |

(52) U.S. Cl.
CPC ............. *H04N 5/33* (2013.01); *H04N 13/161* (2018.05); *H04N 13/194* (2018.05); *H04N 13/239* (2018.05); *H04N 13/346* (2018.05); *A61B 2090/373* (2016.02); *A61B 2090/502* (2016.02); *G02B 2027/014* (2013.01); *G02B 2027/0134* (2013.01); *G02B 2027/0138* (2013.01)

(58) Field of Classification Search
CPC .. H04N 5/33; A61B 90/361; A61B 2090/373; A61B 2090/502; A61B 2090/3618; A61B 90/37; G02B 27/0172; G02B 2027/0134; G02B 2027/0138; G02B 2027/014; G02B 27/141; G02B 2027/0132
USPC .......................................................... 348/43
See application file for complete search history.

(56) References Cited

U.S. PATENT DOCUMENTS

| | | | |
|---|---|---|---|
| 2014/0340287 A1* | 11/2014 | Achilefu | H04N 13/344 345/8 |
| 2015/0043003 A1 | 2/2015 | Chung et al. | |
| 2015/0257735 A1* | 9/2015 | Ball | A61B 5/0035 600/440 |
| 2017/0318235 A1* | 11/2017 | Schneider | G06K 9/00664 |

FOREIGN PATENT DOCUMENTS

| | | |
|---|---|---|
| KR | 10-2015-0012243 A | 2/2015 |
| KR | 10-2017-0020186 A | 2/2017 |
| WO | 2014/004717 A2 | 1/2014 |

\* cited by examiner (a)

(b)

(a)

(b)

(c)

HEAD MOUNT SYSTEM FOR PROVIDING SURGERY SUPPORT IMAGE

TECHNICAL FIELD

The present invention relates to a head mount system for providing a surgery support image and, more particularly, to a head mount system for providing a surgery support image enabling a surgeon to more accurately identify a surgical site through a near-infrared image.

BACKGROUND ART

A sentinel lymph node (SLN) is a lymph node where cancer cells in a primary tumor are first metastasized, the sentinel lymph node being an important indicator to determine whether metastasis to lymph nodes occurs. Accordingly, when no cancer cells are found through biopsy of sentinel lymph nodes, other lymph nodes are determined to have no metastases, and thus no further surgery is required to be performed.

When performing a sentinel lymph node biopsy in vivo through accurate screening of sentinel lymph nodes, which is the important indicator in determining whether cancer metastasis has occurred, postoperative complications such as lymphedema may be lessened and scarring on a patient's body may be minimized. For this reason, in early breast cancer or melanoma surgery, a screening method for sentinel lymph nodes by using a targeted drug is used as a standard technique.

As the screening method for sentinel lymph node in a patient's body by using the targeted drug, there are provided methods such as a method of obtaining a visible light image by using a blue dye and a visible light camera, a method of obtaining a near-infrared fluorescence image by using a near-infrared fluorescent dye and a near-infrared camera, and a method of obtaining a radiographic image by imaging a radiopharmaceutical, which is accumulated in sentinel lymph nodes, with a gamma imaging device.

Recently, among near-infrared fluorescent dyes, Indocyanine Green (IOG) has been approved by the FDA, and the screening of sentinel lymph nodes by using a near-infrared fluorescent dye has been prepared for clinical use.

Meanwhile, in the case where surgery to remove an actual tumor is performed along with an accurate screening of sentinel lymph nodes as described above, when a surgeon performs surgery while looking at a surgical site of a real patient, the screened sentinel lymph nodes as described above and the actual surgical site of the real patient should be matched to determine an extent to be excised.

In this regard, when some of sentinel lymph nodes having metastasized cancer cells remain without being excised, the metastasis of the cancer cells occurs after surgery, causing a problem of performing reoperation; and when excision is performed in a wide extent more than necessary, there is a problem in that the quality of life of a patient is decreased due to degradation in the function of the corresponding organs. Therefore, an accurate screening of sentinel lymph nodes as well as accurate excision should be performed during surgery.

Accordingly, a method of injecting a near-infrared fluorescent dye into cancer cells during surgery, imaging a surgical site with a visible light camera and a near-infrared fluorescent camera, matching a visible image to a near-infrared image, and displaying the matched image on a monitor installed in an operating room has been proposed.

Meanwhile, as shown in FIG. 1, a surgeon checks a fluorescence image area displayed on a monitor 10 installed in the operating room with the naked eyes, and once again, performs surgery while looking at a surgical site of a patient lying on an operating table, and thus there is inconvenience of taking turns looking at the two spots to perform the surgery. In particular, there is a limitation in that accurate excision may not be achieved because the part dyed with fluorescence is not identified when looking at the actual surgical site of the patient.

In order to solve this problem, in Korean Patent No. 10-1355348, in the "SURGICAL OPERATION GUIDE SYSTEM AND METHOD THEREFOR", a technique is disclosed, in which an image of a patient's lesion, taken by CT, MRI, and X-ray, is displayed on a transparent display in the form of glasses worn by a surgeon, and the surgeon performs surgery while looking at the image of the lesion displayed on the transparent display together with the actual lesion visible through the transparent display.

In the method disclosed in Korean Patent No. 10-1355348, a gyro sensor is used, or an image of the lesion is converted using a specific part of a patient as a reference point in order to match the pre-captured image of the lesion to the actual image that the surgeon sees through the transparent display.

However, when detecting movement of the surgeon by using the gyro sensor, there is a disadvantage in that it is difficult for the lesion image to be matched to the actual image accurately due to inability to reflect the patient's movement.

In addition, in the case of using a pre-captured lesion image, when a positional change occurs in the patient's surgical site, that is, when the lesion, an organ, or the like is moved during the surgery, the lesion image does not accurately match to the actual lesion, and thus there is a possibility that the surgeon may be hindered to accurately identify the lesion.

In this regard, in the method of providing a surgery support image using "SMART GLASSES SYSTEM FOR SUPPLYING SURGERY ASSIST IMAGE AND METHOD FOR SUPPLYING SURGERY ASSIST IMAGE USING SMART GLASSES", which is disclosed in Korean Patent No. 10-1667152 filed by the inventor of the present invention, a near-infrared image and a visible light image respectively captured by the near-infrared camera and the visible light camera are used, and the capturing direction and size of the near-infrared image are converted based on the visible light image and displayed on a screen of the smart glass, whereby the near-infrared image displayed on the screen of the smart glass overlaps the surgical site actually seen by a surgeon, and thus the near-infrared fluorescence image provides the same effect as though displayed on the actual surgical site of a patient.

However, in Korean Patent No. 10-1667152, both near-infrared and visible light cameras should be used, and since the direction, position, etc. of the near-infrared camera are different from those of the line of vision of the surgeon, an image processing procedure using visible light image should be performed in order to adjust the difference, and thus there is inconvenience in that the structure is rather complicated and image processing technology should be applied thereto.

DISCLOSURE

Technical Problem

In this regard, the present invention has been devised to solve the above problems, and the objective of the present invention is to provide a head mount system enabling image capturing near-infrared light from the same line of vision of a user, like a surgeon, and providing a surgery support image that allows an image processing procedure as well as a mechanical structure to be simplified by excluding the use of visible light camera or smart glasses.

Technical Solution

According to the present invention, the objective is achieved by a head mount system for providing a surgery support image, the head mount system including: a head mount body wearable on a user's head; a near-infrared camera installed on the head mount body and capturing near-infrared light; a near-infrared image projection unit installed on the head mount body and projecting a near-infrared image; a near-infrared image processing unit receiving a captured image taken by the near-infrared camera, generating the near-infrared image, and transmitting the near-infrared image to the near-infrared image projection unit; and a transparent optic system installed on the head mount body to be positioned in front of user's eyes when the head mount body is worn on the user's head, transmitting visible light to enable a user to see a user's front, reflecting the near-infrared light coming from the user's front to the near-infrared camera so as to allow the near-infrared camera to capture the near-infrared light, and reflecting the near-infrared image projected from the near-infrared image projection unit to the user's eyes.

Here, the head mount system for providing a surgery support image may further include: a wireless communication part installed in the head mount body to perform wireless communication, wherein the near-infrared image processing unit is installed outside the head mount body, receives the captured image of the near-infrared camera through the wireless communication part, and transmits the near-infrared image to the wireless communication part to deliver the near-infrared image to the near-infrared image projection unit.

In addition, the transparent optic system may include: a left image optical system positioned in front of a user's left eye; and a right image optical system positioned in front of a user's right eye. The near-infrared camera may include: a left image near-infrared camera that captures the near-infrared light coming through the left image optical system; and a right image near-infrared camera that captures the near-infrared light coming through the right image optical system. The near-infrared image projection unit may include: a left image projection unit projecting a near-infrared left image to the left image optical system; and a right image projection unit projecting a near-infrared right image to the right image optical system. The near-infrared image processing unit may use each captured image taken by the left image near-infrared camera and the right image near-infrared camera to respectively generate the near-infrared left image and the near-infrared right image to deliver to the left image projection unit and the right image projection unit.

In addition, the left image optical system may include: a first left image dichroic mirror transmitting the visible light coming from the user's front and reflecting the near-infrared light coming from the user's front to the left image near-infrared camera; and a second left image dichroic mirror disposed at a front or a rear of the first left image dichroic mirror, transmitting the visible light coming from the user's front, and reflecting the near-infrared left image projected from the left image projection unit to the user's eyes. The right image optical system may include: a first right image dichroic mirror transmitting the visible light coming from the user's front and reflecting the near-infrared light coming from the user's front to the right image near-infrared camera; and a second right image dichroic mirror disposed at a front or a rear of the first right image dichroic mirror, transmitting the visible light coming from the user's front, and reflecting the near-infrared right image projected from the right image projection unit to the user's eyes.

In addition, the left image optical system may include: a left image transparent plate made of a transparent material; a first left image dichroic layer coated on a side surface of the left image transparent plate, transmitting the visible light coming from the user's front, and reflecting the near-infrared light coming from the user's front to the left image near-infrared camera; and a second left image dichroic layer coated on an opposite side surface of the left image transparent plate, transmitting the visible light coming from the user's front, and reflecting the near-infrared left image projected from the left image projection unit to the user's eyes. The right image optical system may include: a right image transparent plate made of the transparent material; a first right image dichroic layer coated on a side surface of the right image transparent plate, transmitting the visible light coming from the user's front, and reflecting the near-infrared light coming from the user's front to the right image near-infrared camera; and a second right image dichroic layer coated on an opposite side surface of the right image transparent plate, transmitting the visible light coming from the user's front, and reflecting the near-infrared right image projected from the right image projection unit to the user's eyes.

In addition, the left image near-infrared camera may be disposed on either one side of upper and lower parts of the left image optical system, the left image projection unit may be disposed on an opposite side of the upper and lower parts of the left image optical system, the right image near-infrared camera may be disposed on either one side of upper and lower parts of the right image optical system, and the right image projection unit may be disposed on an opposite side of the upper and lower parts of the right image optical system.

In addition, the transparent optic system may include: a left image optical system positioned in front of a user's left eye; and a right image optical system positioned in front of a user's right eye. The near-infrared image projection unit may include: a left image projection unit projecting a near-infrared left image from a left side surface of the left image optical system to the left image optical system; and a right image projection unit projecting a near-infrared right image from a right side surface of the right image optical system to the right image optical system. The near-infrared camera may be disposed at the upper or the lower part between the left image optical system and the right image optical systems.

In addition, the left image optical system may include: a left image dichroic unit transmitting the visible light coming from the user's front, reflecting the near-infrared light coming from the user's front to the right side, and reflecting the near-infrared left image coming from the left image projection unit to the user's eyes; and a left image reflection mirror disposed on the right side of the left image dichroic unit and reflecting the near-infrared light reflected from the left image dichroic unit to the near-infrared camera. The right image optical system may include: a right image dichroic unit transmitting the visible light coming from the user's front, reflecting the near-infrared light coming from the user's front to the left side, and reflecting the near-infrared right image coming from the right image projection unit to the user's eyes; and a right image reflection mirror disposed on the left side of the right image dichroic unit and reflecting the near-infrared light reflected from the right image dichroic unit to the near-infrared camera. The near-infrared image processing unit may divide the captured images taken by the near-infrared cameras and reflected by the left image reflection mirror and the right image reflection mirror to respectively generate the near-infrared left image and the near-infrared right image, and may respectively deliver the near-infrared left image and the near-infrared right image to the left image projection unit and the right image projection unit.

Advantageous Effects

According to the present invention in accordance with the above configuration, there is provided a head mount system for providing a surgery support image that allows a user, such as a surgeon, to visually look at an excision site, in which cancer cells have metastasized, including sentinel lymph nodes, while performing the surgery, in real time.

In addition, a simpler image processing procedure is applicable to generate a near-infrared image by making the line of vision of the surgeon and the capturing line of the near-infrared camera the same through a transparent optic system.

In addition, without using expensive device such as smart glasses, the image projected from a near-infrared image projection unit is directly projected to the user's eyes through the transparent optic system, thereby implementing the head mount system with lower manufacturing cost and a simple structure.

In addition, the left and right images are separately captured, and projected to the left and right eyes of the user, thereby realizing a stereoscopic image.

BEST MODE

The present invention relates to a head mount system for providing a surgery support image, and includes: a head mount body wearable on a user's head; a near-infrared camera installed on the head mount body and capturing near-infrared light; a near-infrared image projection unit installed on the head mount body and projecting a near-infrared image; a near-infrared image processing unit receiving a captured image taken by the near-infrared camera, generating the near-infrared image, and transmitting the near-infrared image to the near-infrared image projection unit; and a transparent optic system installed on the head mount body to be positioned in front of user's eyes when the head mount body is worn on the user's head, transmitting visible light to enable a user to see a user's front, reflecting the near-infrared light coming from the user's front to the near-infrared camera so as to allow the near-infrared camera to capture the near-infrared light, and reflecting the near-infrared image projected from the near-infrared image projection unit to the user's eyes.

MODE FOR INVENTION

Hereinafter, with reference to the accompanying drawings, exemplary embodiments according to the present invention will be described in detail.

Figure 1:
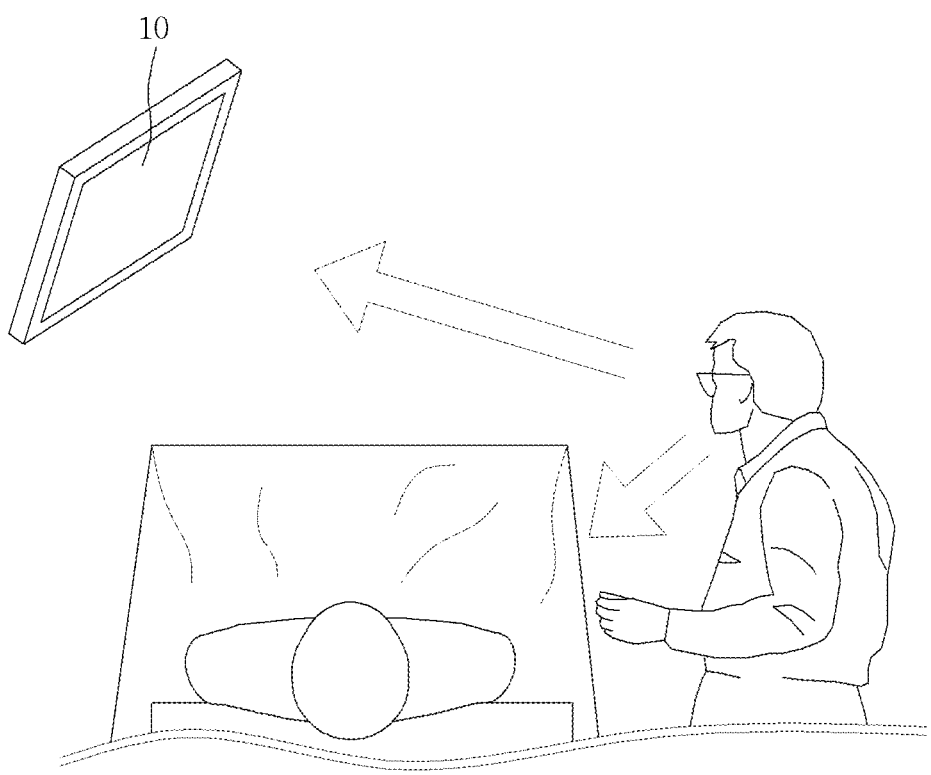
FIG. 1 is a view showing an example of a surgical environment in a conventional operating room.
Figure 2:
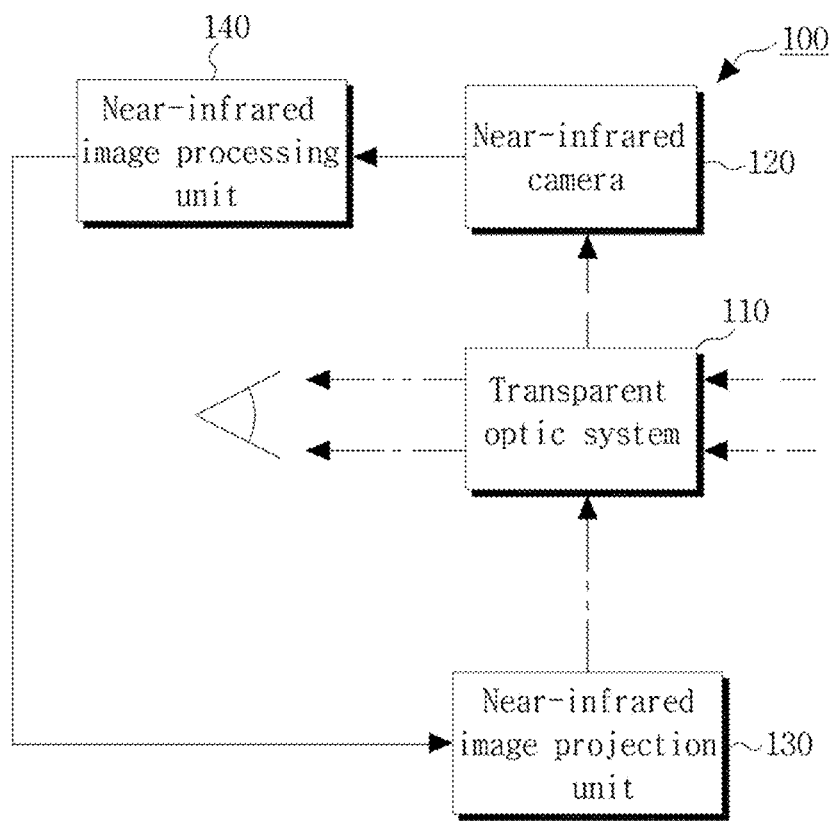
FIG. 2 is a view showing a configuration of a head mount system for providing a surgery support image according to the present invention.

FIG. 2 is a view showing a configuration of a head mount system 100 that provides a surgery support image according to the present invention. Referring to FIG. 2, the head mount system 100 providing the surgery support image according to the present invention (hereinafter referred to as "head mount system 100") includes a near-infrared camera 120, an image projection unit, a near-infrared image processing unit 140, and a transparent optic system 110.

Here, in the present invention, the near-infrared camera 120, the image projection unit, and the transparent optic system 110 are installed on a head mount body wearable on a user's head, and the head mount body having various structure that a user may wear on the head is applicable, and thus a description of the structure thereof will be omitted.

The near-infrared camera 120 is installed on the head mount body to capture near-infrared light. As an example, when a fluorescent material is injected into a patient's surgical site, the fluorescent material becomes capable of being captured by the near-infrared camera 120.

The image projection unit is installed on the head mount body and projects a near-infrared image transmitted from the near-infrared image processing unit 140. Here, the near-infrared image processing unit 140 receives a captured image taken by the near-infrared camera 120, performs image processing of the corresponding captured image to generate a near-infrared image, and transmits the near-infrared image to the near-infrared image projection unit 130.

The transparent optic system 110 is installed on the head mount body to be positioned in front of the user's eyes when the head mount body is worn on the user's head. At this time, the transparent optic system 110 transmits visible light (i.e., one-dotted chain line in FIG. 2) coming from the front of the user so that the user is able to see the front side. Accordingly, even when the user wears the head mount body according to the present invention on the head and the transparent optic system 110 is positioned in front of the user's eyes, it is possible to visually check the front in the same manner as wearing transparent glasses.

In addition, the transparent optic system 110 reflects the near-infrared light (i.e., dotted line in FIG. 2) coming from the user's front to the near-infrared camera 120, so that the near-infrared camera 120 captures the near-infrared light to form a captured image. In addition, the transparent optic system 110 reflects the near-infrared image projected from the near-infrared image projection unit 130 (i.e., the double-dotted chain line in FIG. 2) to the user's eyes, thereby enabling the user to visually check the near-infrared image. Here, the near-infrared image projected through the near-infrared image projection unit 130 is a visualized image of near-infrared light taken by the near-infrared camera 120, and is corresponded to an image in a visible light region, which is visible to the human eyes.

According to the above configuration, the transparent optic system 110 reflects the near-infrared light coming into the user's eyes to the near-infrared camera 120 to capture the near-infrared light, and the near-infrared image processing unit 140 generates the captured image as a near-infrared image, thereby allowing the near-infrared camera 120 to capture near-infrared light in the same direction as that of the user's line of vision. In this regard, the image processing process previously required, as the imaging direction of the near-infrared camera 120 differs from that of the user's line of vision, is made possible to be significantly simplified.

In addition, the near-infrared image projection unit 130 projects the near-infrared image generated by the near-infrared image processing unit 140 to the transparent optic system 110; the transparent optic system 110 reflects the near-infrared image to the user's eyes; and the near-infrared image is formed on the user's eyes, whereby it is possible to obtain the same effect as the near-infrared image is overlapped with visible light coming through the transparent optic system 110, that is, the actual front view seen by the user.

Figure 9:
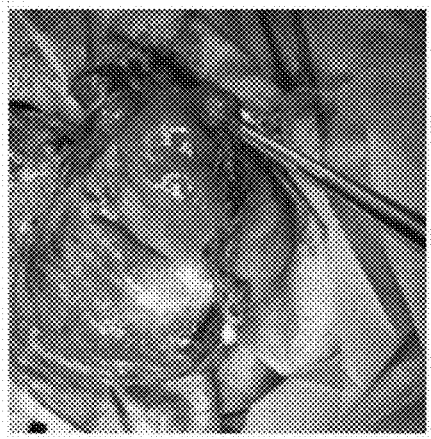
FIG. 9 shows views showing a principle in which a near-infrared image is identified in the head mount system for providing the surgery support image according to the present invention.
Figure 9:
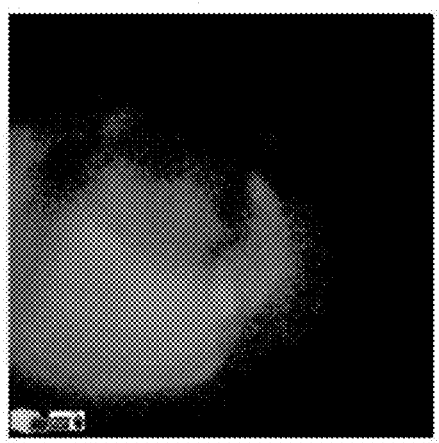
Figure 9:
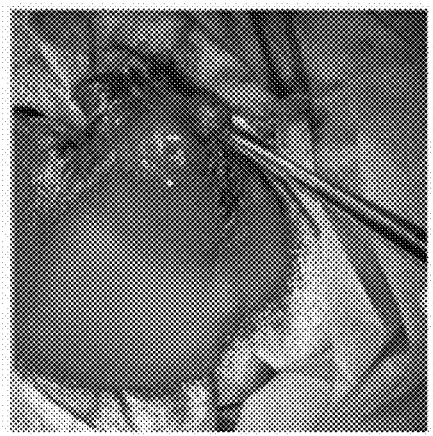

To be more specific, referring to FIG. 9, when the user looks at a patient's surgical site while wearing the head mount body on the head, the patient's surgical site is seen as shown in (a) of FIG. 9. In addition, the captured image taken by the near-infrared camera 120 is as shown in (b) of FIG. 9. At this time, the near-infrared image processing unit 140 extracts only the fluorescence region to generate a near-infrared image, and when the near-infrared image projection unit 130 projects the near-infrared image to form an image in the user's eyes, the user visually recognizes the image as a state where the near-infrared image is overlapped on the actual surgical site, as illustrated in (c) of FIG. 9.

Accordingly, the user recognizes the same as the fluorescent material is painted on the actual surgical site, and even when the user moves during surgery, the near-infrared camera 120 captures an image in the same direction as the user's line of vision by the transparent optic system 110, thereby allowing the near-infrared image to be overlapped at a more accurate position.

Figure 3:
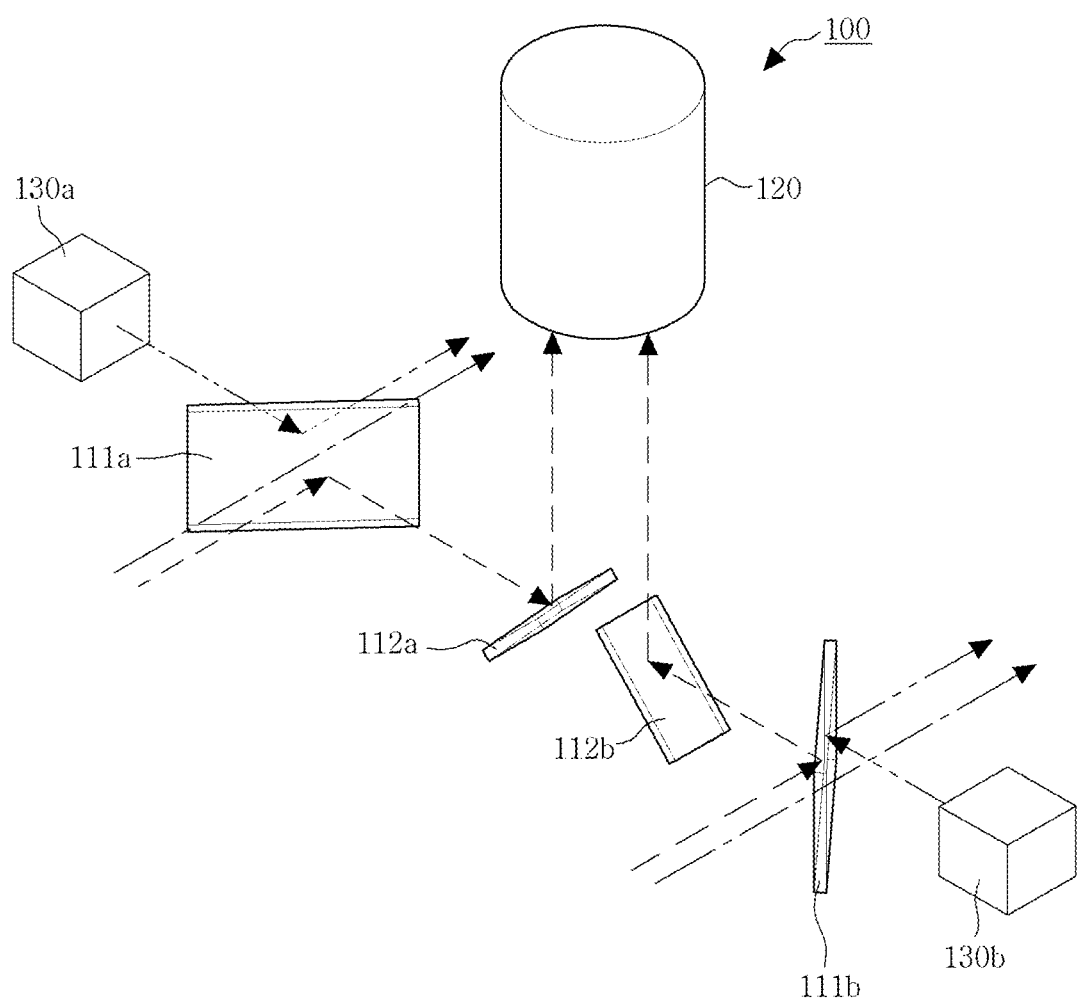
FIGS. 3 and 4 are views showing an example of implementing a head mount system for providing a surgery support image according to a first exemplary embodiment of the present invention.
Figure 4:
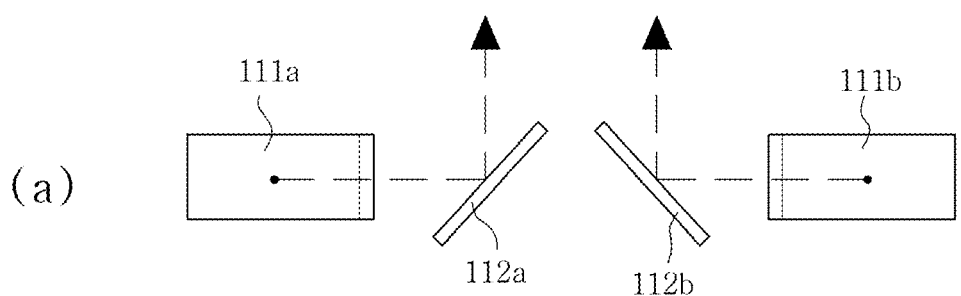
Figure 4:
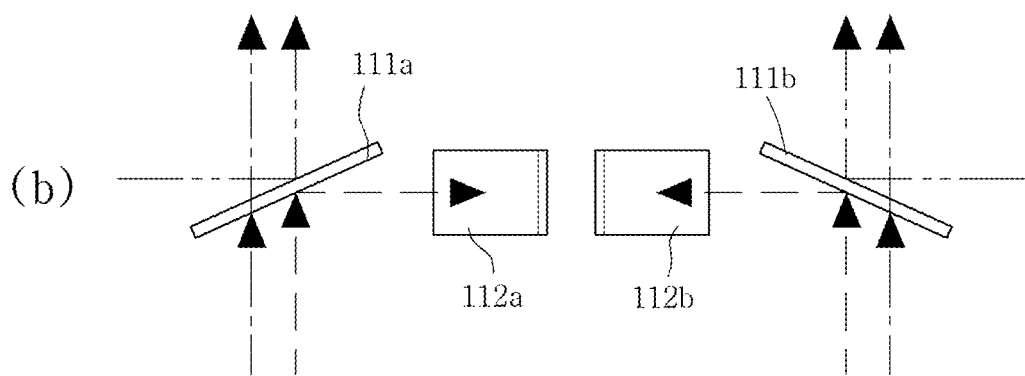

Hereinafter, an example in which the head mount system 100 according to the first exemplary embodiment of the present invention is implemented will be described with reference to FIGS. 3 and 4. Here, (a) of FIG. 4 is a front view of the transparent optic system 110 of FIG. 3 as viewed from the front, and (b) of FIG. 4 is a plan view of the transparent optic system 110 of FIG. 3 as viewed from the top. FIGS. 3 and 4, the dotted line represents visible light, the one-dotted chain line indicates near-infrared light, and the double-dotted chain line indicates the near-infrared image projected from the near-infrared image projection unit 130.

In the examples shown in FIGS. 3 and 4, the head mount system 100, according to the first exemplary embodiment of the present invention, is applied with a single near-infrared camera 120, and the near-infrared image projection unit 130 includes a left image projection unit 130*b* and a right image projection unit 130*a*, as an example.

In addition, as shown in FIGS. 3 and 4, the transparent optic system 110 includes left image optical systems 111*b* and 112*b* and right image optical systems 111*a* and 112*a*. Here, when the user wears the head mount body on the head, the left image optical systems 111*b* and 112*b* are positioned in front of the user's left eye, and the right image optical systems 111*a* and 112*a* are positioned in front of the user's right eye.

The left image projection unit 130*b* of the near-infrared image projection unit 130, as shown in FIG. 3, projects a near-infrared left image from the left side of the left image optical systems 111*b* and 112*b* to the left image optical systems 111*b* and 112*b*, and the right image projection unit 130*a* projects a near-infrared right image from the right side of the right image optical systems 111*a* and 112*a* to the right image optical systems 111*a* and 112*a*.

The near-infrared camera 120 is disposed on the upper or lower part between the left image optical systems 111*b* and 112*b*, and the right image optical systems 111*a* and 112*a*, and in the present invention, as shown in FIG. 3, the near-infrared camera 120 is taken to be positioned at the upper part, as an example.

Here, in the first exemplary embodiment of the present invention, the left image optical systems 111*b* and 112*b* include a left image dichroic unit 111*b* and a left image reflection mirror 112*b*, as an example. The left image dichroic unit 111*b* transmits the visible light coming from the front of the user, thereby enabling the user to see the front with the left eye. In addition, the left image dichroic unit 111*b* reflects the near-infrared light coming from the front of the user to the right side. At this time, the left image reflection mirror 112*b* is disposed on the right side of the left image dichroic unit 111*b* to reflect the near-infrared light reflected from the left image dichroic unit 111*b* to the near-infrared camera 120. Accordingly, the near-infrared camera 120 positioned at the upper part between the left image optical systems 111*b* and 112*b* and the right image optical systems 111*a* and 112*a* is able to capture near-infrared light entering the user's left eye.

In addition, the left image dichroic unit 111*b* reflects the near-infrared left image coming from the left image projection unit 130*b* disposed on the left side to the user's eyes, so that the the near-infrared left image is overlapped in the user's left eye and becomes recognizable.

Similarly, in the first exemplary embodiment of the present invention, the right image optical systems 111*a* and 112*a* include a right image dichroic unit 111*a* and a right image reflection mirror. The right image dichroic unit 111*a* transmits the visible light coming from the user's front, thereby enabling the user to see the front with the right eye. In addition, the right image dichroic unit 111*a* reflects the near-infrared light coming from the front of the user to the left side. At this time, the right image reflection mirror is disposed on the left side of the right image dichroic unit 111*a* to reflect the near-infrared light reflected from the right image dichroic unit 111*a* to the near-infrared camera 120. Accordingly, the near-infrared camera 120 positioned at the upper part between the left image optical systems 111*b* and 112*b* and the right image optical systems 111*a* and 112*a* is able to capture near-infrared light entering the user's right eye.

In addition, the right image dichroic unit 111*a* reflects the near-infrared right image coming from the right image projection unit 130*a* disposed on the right side to the user's eyes, so that the near-infrared right image is overlapped in the user's right eye and becomes recognizable.

Here, in the near-infrared camera 120, as described above, both the near-infrared light coming in the direction of the user's left eye and the near-infrared light coming in the direction of the user's right eye are all captured, and through adjusting the lens magnification of the near-infrared camera 120, the field of view the user sees with both eyes, especially the surgical site, may be all included.

In addition, the near-infrared image processing unit 140 divides the captured images taken by the near-infrared cameras and reflected by the left image reflection mirror and the right image reflection mirror to respectively generate the near-infrared left image and the near-infrared right image. In addition, the near-infrared image processing unit 140 respectively delivers the generated near-infrared left image and near-infrared right image to the left image projection unit 130b and the right image projection unit 130a. In addition, when the left image projection unit 130b and the right image projection unit 130a respectively project the near-infrared left image and the near-infrared right image to the left image dichroic unit 111b and the right image dichroic unit 111a, the near-infrared left image and the near-infrared right image respectively overlap in the user's left eye and right eye, thereby being recognizable as though the fluorescent material is displayed on the user's surgical site, as shown in (c) of FIG. 9.

In the configuration of the left image dichroic unit 111b and the right image dichroic unit 111a according to the first exemplary embodiment of the present invention, a configuration of the left image optical systems 111b and 112b and the right image optical systems 111a and 112a, of the second and third exemplary embodiments of the present invention, may be applied, and thus a detailed description thereof will be described later.

Hereinafter, an example of implementing a head mount system 300 according to the second exemplary embodiment of the present invention will be described with reference to FIGS. 5 and 6. Here, FIG. 6 shows side views of the transparent optic systems 311a and 311b of FIG. 5 viewed from the side. In addition, in FIGS. 5 and 6, the dotted line represents visible light, the one-dotted chain line indicates near-infrared light, and the double-dotted chain line indicates the near-infrared image projected from the near-infrared image projection units 330a and 330b.

The transparent optic systems 311a and 311b according to the second exemplary embodiment of the present invention may include a left image optical system 311b and a right image optical system 311a. As in the first exemplary embodiment, when a user wears a head mount body on the head, the left image optical system 311b and the right image optical systems 111a and 112a are respectively positioned in front of the user's left eye and right eye.

Figure 5:
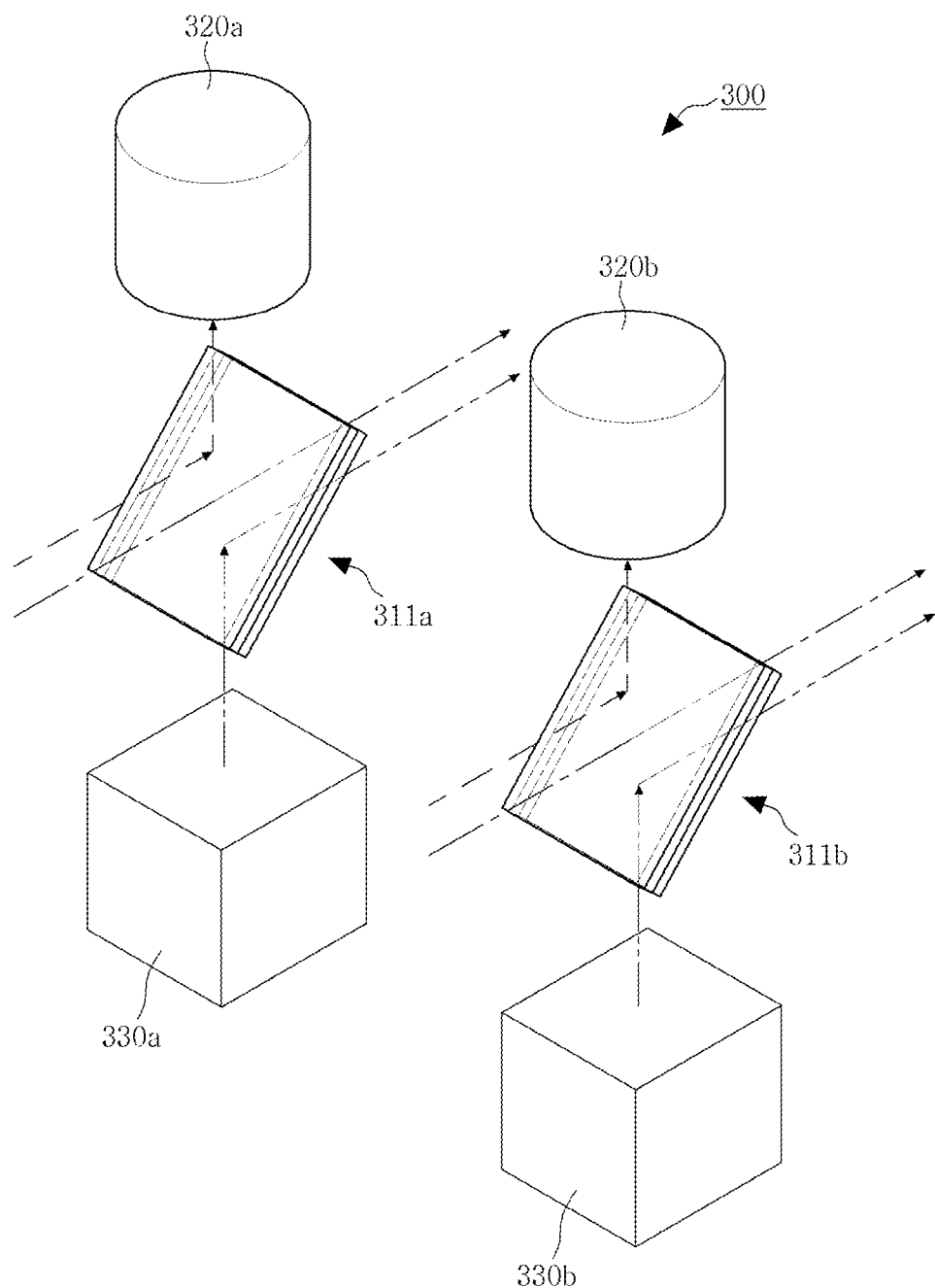
FIGS. 5 and 6 are views showing an example of implementing a head mount system for providing a surgery support image according to a second exemplary embodiment of the present invention.
Figure 6:
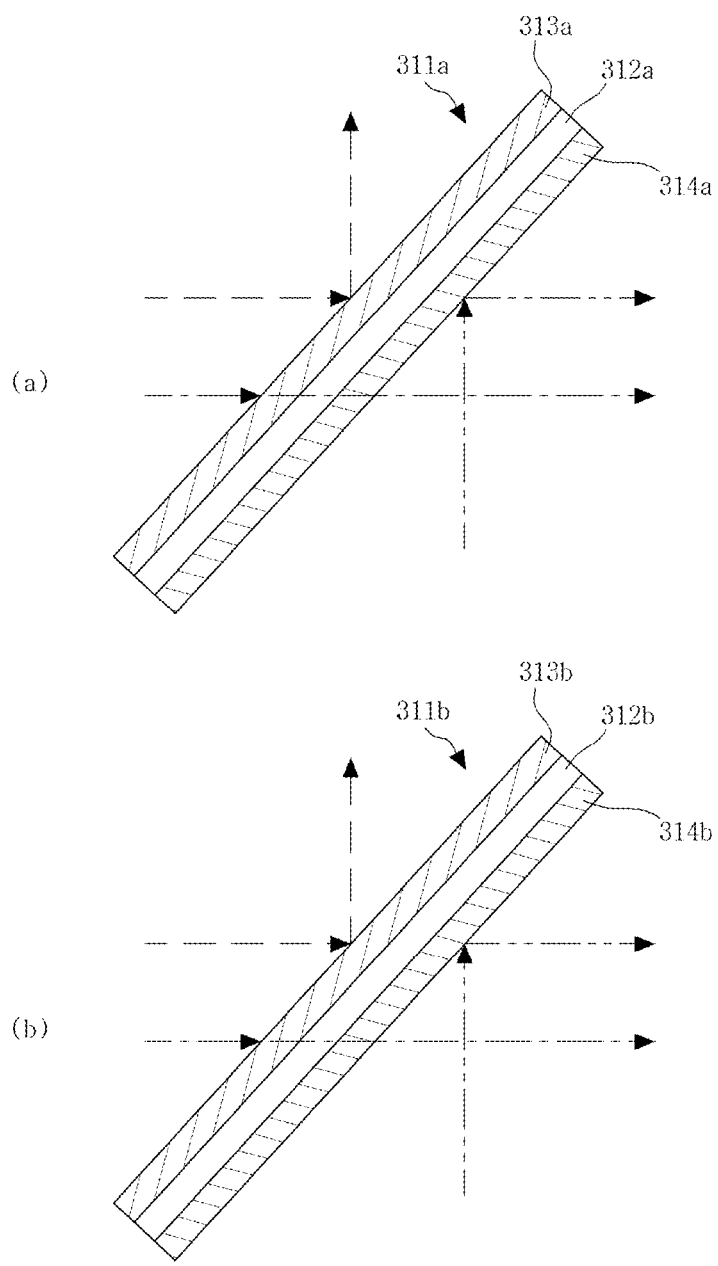

As shown in the FIG. 5, the near-infrared cameras 320a and 320b may include a left image near-infrared camera 320b and a right image near-infrared camera 320a, as shown in FIG. 5. The left image near-infrared camera 320b captures near-infrared light coming through the left image optical system 311b, and the right image near-infrared camera 320a captures near-infrared light coming through the right image optical systems 111a and 112a.

The near-infrared image projection units 330a and 330b may include a left image projection unit 330b and a right image projection unit 330a. The left image projection unit 330b projects the near-infrared left image transmitted from the near-infrared image processing unit 140 to the left image optical system 311b. In addition, the right image projection unit 330a projects the right near-infrared image transmitted from the near-infrared image processing unit 140 to the right image optical systems 111a and 112a.

The near-infrared image processing unit 140 generates a near-infrared left image by using the captured image taken by the left image near-infrared camera 320b and transmits the near-infrared left image to the left image projection unit 330b. Here, the near-infrared light captured by the left image near-infrared camera 320b is the near-infrared light coming in the direction of the user's left eye, and the near-infrared left image generated through this corresponds to the image entering the user's left eye.

Likewise, the near-infrared image processing unit 140 generates a near-infrared right image by using the captured image taken by the right image near-infrared camera 320a and transmits the near-infrared right image to the right image projection unit 330a. Here, the near-infrared light taken by the right image near-infrared camera 320a is the near-infrared light coming in the direction of the user's right eye, and the near-infrared right image generated through this corresponds to the image entering the user's right eye.

According to the above configuration, the left image projection unit 330b and the right image projection unit 330a respectively project the near-infrared left image and the near-infrared right image to the left image optical system 311b and the right image optical systems 111a and 112a; and the near-infrared left image and the near-infrared right image, respectively reflected from the left image optical system 311b and the right image optical systems 111a and 112a, are respectively formed in the left and right eyes of the user, whereby the user is able to recognize as though the fluorescent material is displayed on the surgical site that is directly looked at by oneself.

Here, as shown in FIGS. 5 and 6, the left image optical system 311b according to the second exemplary embodiment of the present invention includes a left image transparent plate 312b, a first left image dichroic layer 313b, and a second left image dichroic layer 314b, as an example. That is, a shape is provided, in which the dichroic mirrors form a layer on both sides of the transparent plate. Here, the left image transparent layer is made of a transparent material, and both visible light and near-infrared light are transmitted.

The first left image dichroic layer 313b is coated on one side surface of the left image transparent plate 312b. In the present invention, for example, the first left image dichroic layer 313b is coated on the front of the left image transparent plate 312b, and the second left image dichroic layer 314b is coated on the rear thereof. However, there is no problem even though the direction is changed.

Here, the first left image dichroic layer 313b transmits the visible light coming from the user's front and reflects the near-infrared light coming from the user's front to the left image near-infrared camera 320b.

The second left image dichroic layer 314b is coated on the other side surface of the left image transparent plate 312b. Here, the second left image dichroic layer 314b transmits the visible light coming from the user's front, and reflects the near-infrared left image projected from the left image projection unit 330b to the user's eyes.

Similarly, the right image optical systems 111a and 112a according to the second exemplary embodiment of the present invention, as shown in FIGS. 5 and 6, include a right image transparent plate 312a, a first right image dichroic layer 313a, and a second right image dichroic layer 314a, as an example. That is, like the left image optical system, a shape is provided, in which the dichroic mirrors form a layer on both sides of the transparent plate. Here, the right image transparent layer is made of a transparent material, and both visible light and near-infrared light are transmitted.

The first right image dichroic layer 313a is coated on one side surface of the right image transparent plate 312a. In the present invention, for example, the first right image dichroic layer 313a is coated on the front of the right image transparent plate 312a, and the second right image dichroic layer 314a is coated on the rear thereof. However, there is no problem even though the direction is changed.

Here, the first right image dichroic layer 313a transmits the visible light coming from the user's front, and reflects the near-infrared light coming from the user's front to the right image near-infrared camera 320a.

The second right image dichroic layer 314a is coated on the other side surface of the right image transparent plate 312a. Here, the second right image dichroic layer 314a transmits the visible light coming from the user's front, and reflects the near-infrared right image projected from the right image projection unit 330a to the user's eyes.

According to the above configuration, it is possible to capture near-infrared light in the same direction as that of the user's line of vision, and the near-infrared light coming into the left and right eyes are respectively captured by the left image near-infrared camera 320b and the right image near-infrared camera 320a, thereby being formed into a near-infrared left image and a near-infrared right image in the user's eyes. Therefore, it is possible to obtain an effect as though a more three-dimensional near-infrared image is displayed on the actual surgical site, as shown in the above-described exemplary embodiment.

Here, the configuration of the left image optical system 311b and the right image optical systems 111a and 112a according to the second exemplary embodiment of the present invention may be respectively applied to the left image dichroic unit 111b and the right image dichroic unit 111a, of the first exemplary embodiment described above, and in this regard, the arrangement has a structure as shown in FIG. 3.

Hereinafter, an example of implementing a head mount system 500 according to the third exemplary embodiment of the present invention will be described with reference to FIGS. 7 and 8. Here, FIG. 8 shows side views of transparent optic systems 511a and 511b of FIG. 7 viewed from the side. In addition, in FIGS. 7 and 8, the dotted line indicates visible light, the one-dotted chain line indicates near-infrared light, and double-dotted chain line indicates near-infrared image projected from the near-infrared image projection units 530a and 530b.

Here, the head mount system 500 according to the third exemplary embodiment of the present invention corresponds to the configuration of the second exemplary embodiment, and examples of the configuration of the transparent optic systems 511a and 511b are different, and thus a configuration of the transparent optic systems 511a and 511b will be described in detail.

The transparent optic systems 511a and 511b according to the third exemplary embodiment of the present invention may include left image optical systems 513b and 514b and right image optical systems 513a and 514a. As in the first and second exemplary embodiments, when the user wears the head mount body on the head, the left image optical systems 513b and 514b and the right image optical systems 513a and 514a are respectively positioned in front of the left and right eyes of the user.

Figure 7:
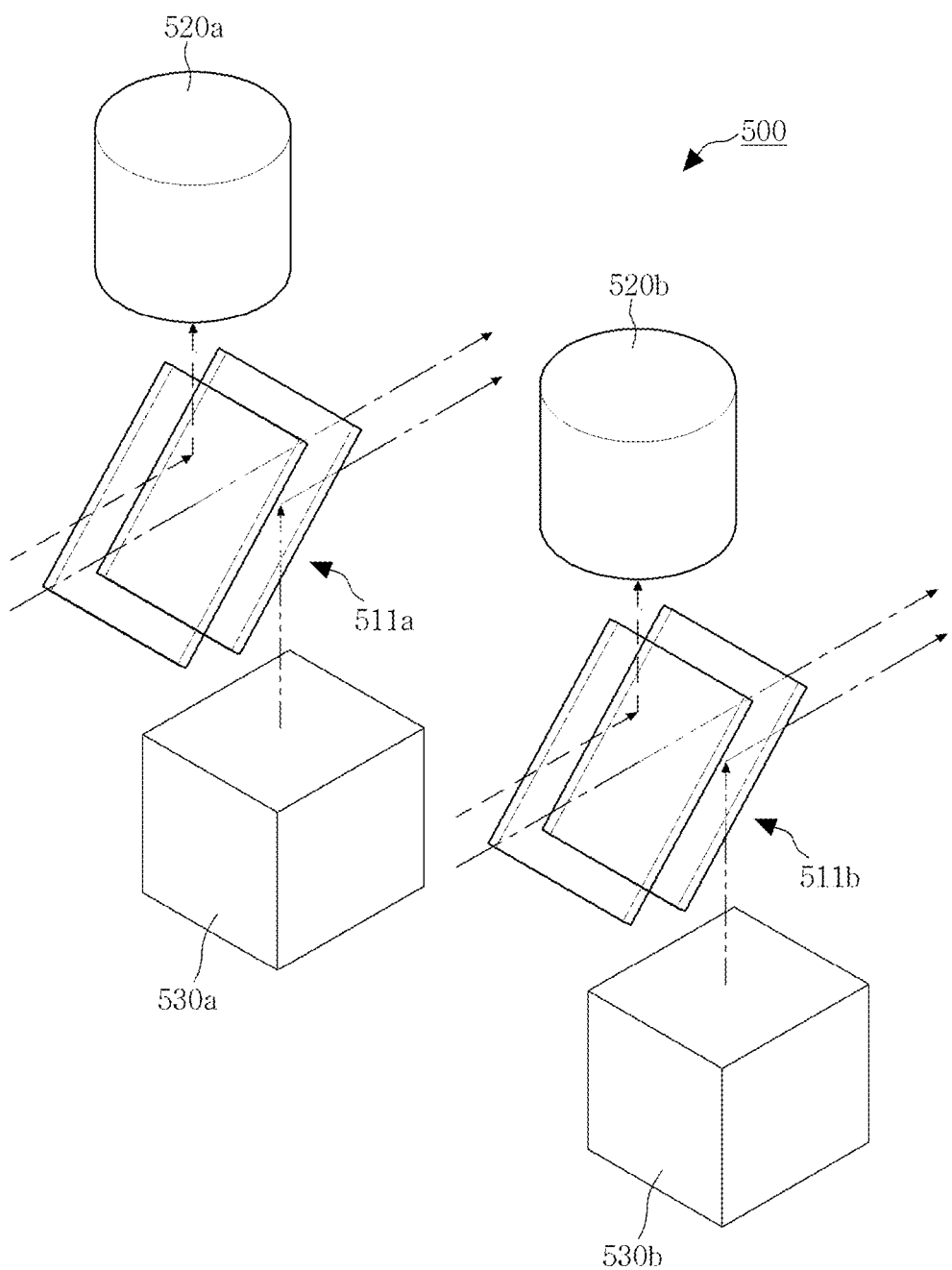
FIGS. 7 and 8 are views showing an example of implementing a head mount system for providing a surgery support image according to a third exemplary embodiment of the present invention.
Figure 8:
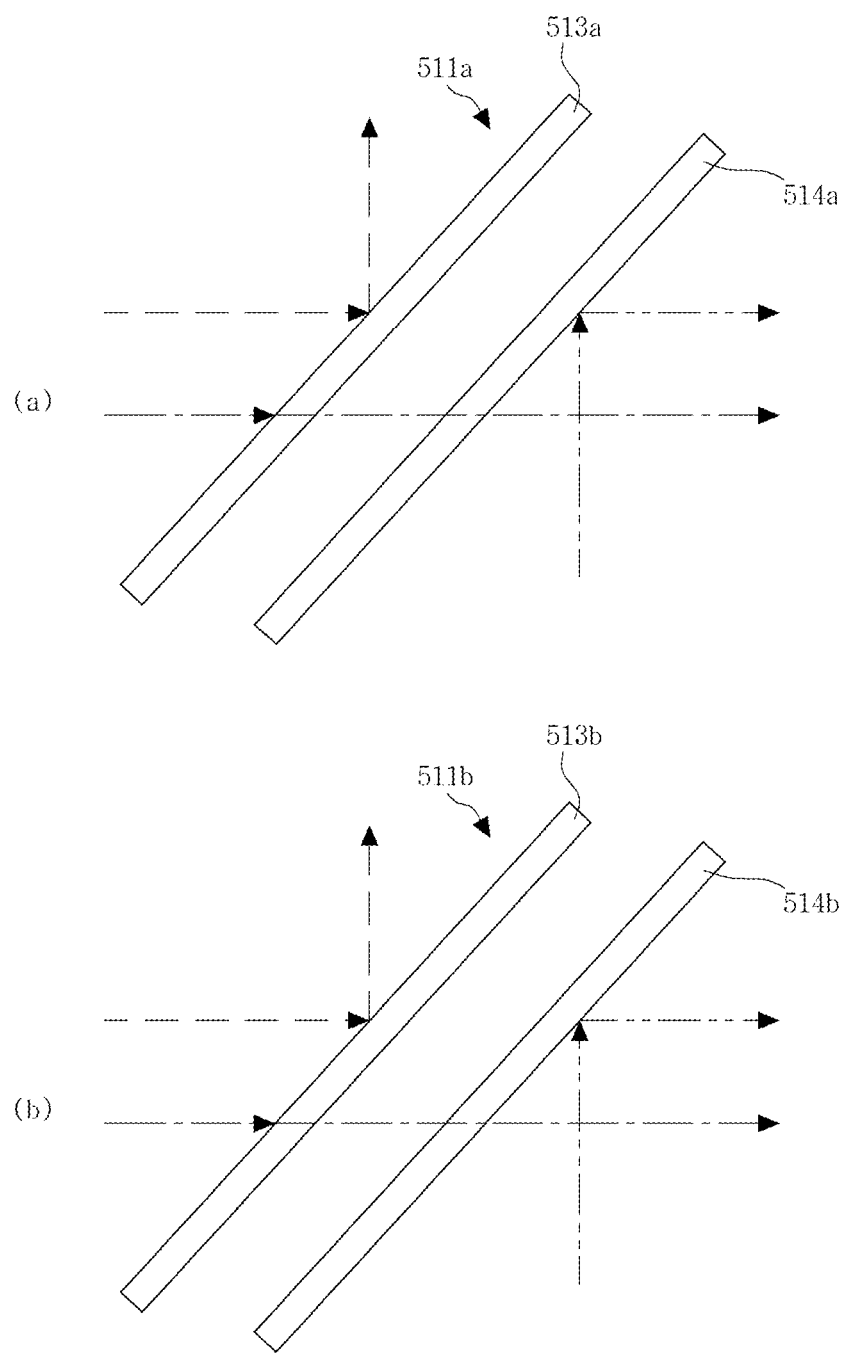

Here, as shown in FIGS. 7 and 8, the left image optical systems 513b and 514b according to the third exemplary embodiment of the present invention may include a first left image dichroic mirror 513b and a second left image dichroic mirror 514b. In the present invention, the first left image dichroic mirror 513b and the second left image dichroic mirror 514b are exemplified as being spaced apart at a regular interval, however, there is no problem even though the mirrors are in contact with each other.

The first left image dichroic mirror 513b transmits the visible light coming from the user's front and reflects the near-infrared light coming from the user's front to a left image near-infrared camera 520b. In addition, the second left image dichroic mirror 514b transmits the visible light coming from the front of the user, and reflects the near-infrared left image projected from the left image projection unit 530b to the user's eyes.

Similarly, as shown in FIGS. 7 and 8, the right image optical systems 513a and 514a according to the third exemplary embodiment of the present invention may include a first right image dichroic mirror 513a and a second right image dichroic mirror 514a. In the present invention, the first right image dichroic mirror 513a and the second right image dichroic mirror 514a are exemplified as being spaced apart at a regular interval. However, there is no problem even though the mirrors are in contact with each other.

The first right image dichroic mirror 513a transmits the visible light coming from the user's front, and reflects the near-infrared light coming from the user's front to a right image near-infrared camera 520a. In addition, the second right image dichroic mirror 514a transmits the visible light coming from the front of the user, and reflects the near-infrared right image projected from the right image projection unit 530a to the user's eyes.

Here, the positions of the left image near-infrared camera 520b and the left image projection unit 530b respectively positioned at the upper part and the lower part of the left image optical systems 513b and 514b are adjustable according to the positions of the first left image dichroic mirror 513b and the second left image dichroic mirror 514b, and the positions of the right image near-infrared camera 520a and the right image projection unit 530a are also equally adjustable.

According to the above configuration, it is possible to capture near-infrared light in the same direction as that of the user's line of vision, and the near-infrared light coming into the left and right eyes are respectively captured by the left image near-infrared camera 520b and the right image near-infrared camera 520a, so that a near-infrared left image and a near-infrared right image are formed in the user's eye. Therefore, it is possible to obtain an effect as though a more three-dimensional near-infrared image is displayed on the actual surgical site, as shown in the above-described exemplary embodiment.

Here, the configurations of the left image optical systems 513b and 514b and the right image optical systems 513a and 514a according to the third exemplary embodiment of the present invention may be respectively applied to the left image dichroic unit 111b and the right image dichroic unit 111a, of the first exemplary embodiment described above, and in this regard, the arrangement has a structure as shown in FIG. 3.

In the above-described second and third exemplary embodiments, the left image near-infrared cameras 320b and 520b and the right image near-infrared cameras 320a and 520a are positioned at the upper part of the transparent optic systems 311a, 311b, 511a, and 511b; and the left image projection units 330b and 530b, and the right image projection units 330a and 530a are positioned at the lower part of the transparent optic systems 311a, 311b, 511a, and 511b, as an example. However, it is apparent that the positions may be changed.

In the above-described exemplary embodiments, it is described that the near-infrared image processing unit 140 transmits an image to the near-infrared image projection unit 130, 130a, 130b, 330a, 330b, 530a, and 530b; and the captured image taken by the near-infrared cameras 120, 320a, 320b, 520a, and 520b is transmitted to the near-infrared image processing unit 140. In the present invention, although the near-infrared image processing unit 140 is installed on the head mount body as an example, in a state where a wireless communication part (not shown) is installed in the head mount body and the near-infrared image processing unit 140 is installed outside the head mount body, that is, for example, in a state where the near-infrared image processing unit 140 is implemented in software or hardware in a computer, etc., it is apparent that the near-infrared cameras 120, 320a, 320b, 520a, and 520b and the near-infrared image projection units 130, 130a, 130b, 330a, 330b, 530a, and 530b may be provided so that these cameras and projection units are connected to each other through the wireless communication part.

Figure 10:
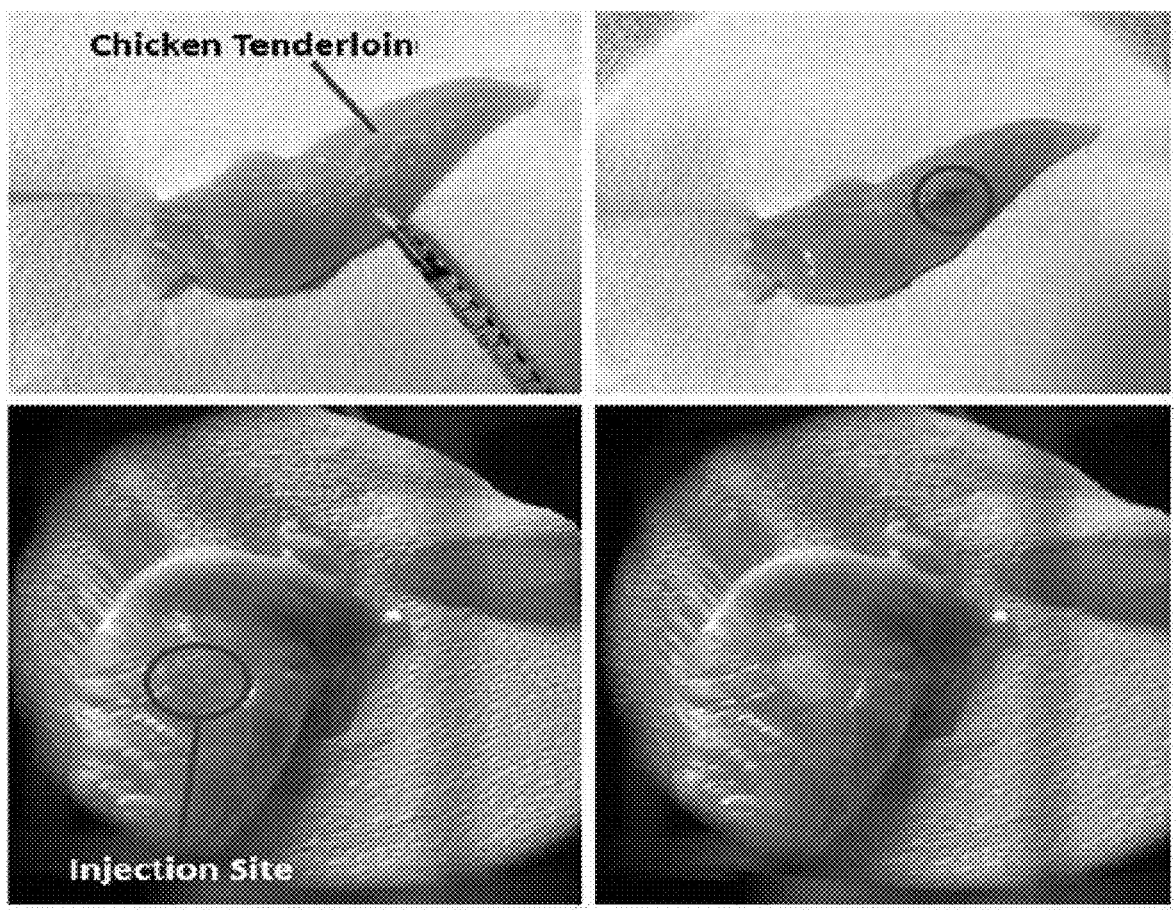
FIG. 10 is a view showing an example of an experiment using the head mount system for providing the surgery support image according to the present invention.

FIG. 10 is a view showing an example of an experiment using the head mount system for providing the surgery support image according to the present invention. As shown in the upper left side of FIG. 10, the experiment is performed by injecting a fluorescent molding agent into a model using chicken breast tenderloin. The upper right side of FIG. 10 is a view showing a state in which the fluorescent molding agent is injected.

The lower left side of FIG. 10 is a view showing an actual visual field image of the surgery, and the lower right side is a view showing a displayed image of the projected near-infrared fluorescence image. Through this, it may be confirmed that the above-described effect is provided through the head mount system for providing the surgery support image according to the present invention.

Although some exemplary embodiments of the present invention have been illustrated and described, it will be understood that those skilled in the art to which the present invention pertains may modify the present exemplary embodiment without departing from the principles or spirit of the present invention. The scope of the invention will be defined by the appended claims and their equivalents.

DESCRIPTION OF THE REFERENCE NUMERALS IN THE DRAWINGS 100, 300, 500: head mount systems 110: transparent optic system
111a: right image dichroic unit 111b: left image dichroic unit
112a: right image reflection mirror 112b: left image reflection mirror
120: near-infrared camera 130: near-infrared image projection unit
130a, 330a, 530a: right image projection units 130b, 330b, 530b: left image projection units
311a, 511a: right image optical systems 311b, 511b: left image optical systems
312a: right image transparent plate 312b: left image transparent plate
313a: first right image dichroic layer 313b: first left image dichroic layer
314a: second right image dichroic layer 313b: second left image dichroic layer
320a, 520a: right image near-infrared cameras
320b, 520b: left image near-infrared cameras
513a: first right image dichroic mirror
513b: first left image dichroic mirror
514a: second right image dichroic mirror
514b: second left image dichroic mirror
140: near-infrared image processing unit

INDUSTRIAL APPLICABILITY

The present invention relates to a head mount system for providing a surgery support image, where a surgeon is able to perform surgery while checking a surgical site through a near-infrared image, and thus it is applicable to a surgical system for a patient.

The invention claimed is:

1. A head mount system for providing a surgery support image, the head mount system comprising:
a head mount body wearable on a user's head;
a near-infrared camera installed on the head mount body and capturing near-infrared light;
a near-infrared image projection unit installed on the head mount body and projecting a near-infrared image;
a near-infrared image processing unit receiving a captured image taken by the near-infrared camera, generating the near-infrared image, and transmitting the near-infrared image to the near-infrared image projection unit; and
a transparent optic system installed on the head mount body to be positioned in front of user's eyes when the head mount body is worn on the user's head, transmitting visible light to enable a user to see a user's front, reflecting the near-infrared light coming from the user's front to the near-infrared camera so as to allow the near-infrared camera to capture the near-infrared light, and reflecting the near-infrared image projected from the near-infrared image projection unit to the user's eyes,
wherein the transparent optic system includes:
a left image optical system positioned in front of a user's left eye; and
a right image optical system positioned in front of a user's right eye,
wherein the near-infrared camera includes:
a left image near-infrared camera that captures the near-infrared light coming through the left image optical system;
a right image near-infrared camera that captures the near-infrared light coming through the right image optical system,
wherein the near-infrared image projection unit includes:
a left image projection unit projecting a near-infrared left image to the left image optical system; and
a right image projection unit projecting a near-infrared right image to the right image optical system,
wherein the near-infrared image processing unit uses each captured image taken by the left image near-infrared camera and the right image near-infrared camera to respectively generate the near-infrared left image and the near-infrared right image to deliver to the left image projection unit and the right image projection unit,
wherein the left image optical system includes:
a first left image dichroic mirror transmitting the visible light coming from the user's front and reflecting the near-infrared light coming from the user's front to the left image near-infrared camera; and a second left image dichroic mirror disposed at a front or a rear of the first left image dichroic mirror, transmitting the visible light coming from the user's front, and reflecting the near-infrared left image projected from the left image projection unit to the user's eyes, and wherein the right image optical system includes:

a first right image dichroic mirror transmitting the visible light coming from the user's front and reflecting the near-infrared light coming from the user's front to the right image near-infrared camera; and a second right image dichroic mirror disposed at a front or a rear of the first right image dichroic mirror, transmitting the visible light coming from the user's front, and reflecting the near-infrared right image projected from the right image projection unit to the user's eyes.

2. The head mount system of claim 1, further comprising:

a wireless communication part installed in the head mount body to perform wireless communication, wherein the near-infrared image processing unit is installed outside the head mount body, receives the captured image of the near-infrared camera through the wireless communication part, and transmits the near-infrared image to the wireless communication part to deliver the near-infrared image to the near-infrared image projection unit.

3. A head mount system for providing a surgery support image, the head mount system comprising:

a head mount body wearable on a user's head;

a near-infrared camera installed on the head mount body and capturing near-infrared light;

a near-infrared image projection unit installed on the head mount body and projecting a near-infrared image;

a near-infrared image processing unit receiving a captured image taken by the near-infrared camera, generating the near-infrared image, and transmitting the near-infrared image to the near-infrared image projection unit; and a transparent optic system installed on the head mount body to be positioned in front of user's eyes when the head mount body is worn on the user's head, transmitting visible light to enable a user to see a user's front, reflecting the near-infrared light coming from the user's front to the near-infrared camera so as to allow the near-infrared camera to capture the near-infrared light, and reflecting the near-infrared image projected from the near-infrared image projection unit to the user's eyes, wherein the transparent optic system includes:

a left image optical system positioned in front of a user's left eye; and a right image optical system positioned in front of a user's right eye, wherein the near-infrared camera includes:

a left image near-infrared camera that captures the near-infrared light coming through the left image optical system; and a right image near-infrared camera that captures the near-infrared light coming through the right image optical system, wherein the near-infrared image projection unit includes:

a left image projection unit projecting a near-infrared left image to the left image optical system; and a right image projection unit projecting a near-infrared right image to the right image optical system, wherein the near-infrared image processing unit uses each captured image taken by the left image near-infrared camera and the right image near-infrared camera to respectively generate the near-infrared left image and the near-infrared right image to deliver to the left image projection unit and the right image projection unit, wherein the left image optical system includes:

a left image transparent plate made of a transparent material;

a first left image dichroic layer coated on a side surface of the left image transparent plate, transmitting the visible light coming from the user's front, and reflecting the near-infrared light coming from the user's front to the left image near-infrared camera; and a second left image dichroic layer coated on an opposite side surface of the left image transparent plate, transmitting the visible light coming from the user's front, and reflecting the near-infrared left image projected from the left image projection unit to the user's eyes, and wherein the right image optical system includes:

a right image transparent plate made of the transparent material;

a first right image dichroic layer coated on a side surface of the right image transparent plate, transmitting the visible light coming from the user's front, and reflecting the near-infrared light coming from the user's front to the right image near-infrared camera; and a second right image dichroic layer coated on an opposite side surface of the right image transparent plate, transmitting the visible light coming from the user's front, and reflecting the near-infrared right image projected from the right image projection unit to the user's eyes.

4. The head mount system of claim 1, wherein the left image near-infrared camera is disposed on either one side of upper and lower parts of the left image optical system, the left image projection unit is disposed on an opposite side of the upper and lower parts of the left image optical system, the right image near-infrared camera is disposed on either one side of upper and lower parts of the right image optical system, and the right image projection unit is disposed on an opposite side of the upper and lower parts of the right image optical system.

5. The head mount system of claim 3, wherein the left image near-infrared camera is disposed on either one side of upper and lower parts of the left image optical system, the left image projection unit is disposed on an opposite side of the upper and lower parts of the left image optical system, the right image near-infrared camera is disposed on either one side of upper and lower parts of the right image optical system, and the right image projection unit is disposed on an opposite side of the upper and lower parts of the right image optical system.

6. A head mount system for providing a surgery support image, the head mount system comprising:

a head mount body wearable on a user's head;

a near-infrared camera installed on the head mount body and capturing near-infrared light;

a near-infrared image projection unit installed on the head mount body and projecting a near-infrared image;

a near-infrared image processing unit receiving a captured image taken by the near-infrared camera, generating the near-infrared image, and transmitting the near-infrared image to the near-infrared image projection unit; and a transparent optic system installed on the head mount body to be positioned in front of user's eyes when the head mount body is worn on the user's head, transmitting visible light to enable a user to see a user's front, reflecting the near-infrared light coming from the user's front to the near-infrared camera so as to allow the near-infrared camera to capture the near-infrared light, and reflecting the near-infrared image projected from the near-infrared image projection unit to the user's eyes, wherein the transparent optic system includes:

a left image optical system positioned in front of a user's left eye; and a right image optical system positioned in front of a user's right eye, wherein the near-infrared image projection unit includes:

a left image projection unit projecting a near-infrared left image from a left side surface of the left image optical system to the left image optical system; and a right image projection unit projecting a near-infrared right image from a right side surface of the right image optical system to the right image optical system, wherein the near-infrared camera is disposed at the upper or the lower part between the left image optical system and the right image optical systems, wherein the left image optical system includes:

a left image dichroic unit transmitting the visible light coming from the user's front, reflecting the near-infrared light coming from the user's front to the right side, and reflecting the near-infrared left image coming from the left image projection unit to the user's eyes; and a left image reflection mirror disposed on the right side of the left image dichroic unit and reflecting the near-infrared light reflected from the left image dichroic unit to the near-infrared camera, wherein the right image optical system includes:

a right image dichroic unit transmitting the visible light coming from the user's front, reflecting the near-infrared light coming from the user's front to the left side, and reflecting the near-infrared right image coming from the right image projection unit to the user's eyes; and a right image reflection mirror disposed on the left side of the right image dichroic unit and reflecting the near-infrared light reflected from the right image dichroic unit to the near-infrared camera, and wherein the near-infrared image processing unit divides the captured images taken by the near-infrared cameras and reflected by the left image reflection mirror and the right image reflection mirror to respectively generate the near-infrared left image and the near-infrared right image, and respectively delivers the near-infrared left image and the near-infrared right image to the left image projection unit and the right image projection unit.

* * * * *